(12) United States Patent
Choi et al.

(10) Patent No.: US 10,155,019 B2
(45) Date of Patent: Dec. 18, 2018

(54) METHOD FOR IMPROVING GINGIVITIS AND PERIODONTITIS BY ANTIBACTERIAL, ANTIOXIDANT AND ANTI-INFLAMMATORY EFFECTS AND INHIBITION OF ALVEOLAR BONE LOSS OF COMPLEX EXTRACTS OF MORINGA LEAF AND EUCOMMIA BARK

(71) Applicant: HLSCIENCE CO., LTD., Gyeonggi-do (KR)

(72) Inventors: Beom-Rak Choi, Gyeonggi-do (KR); Hye-Rim Park, Jeollabuk-do (KR); Hae-Yeon Lee, Gyeonggi-do (KR)

(73) Assignee: HLSCIENCE CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/927,464

(22) Filed: Mar. 21, 2018

(65) Prior Publication Data

US 2018/0271925 A1 Sep. 27, 2018

(30) Foreign Application Priority Data

Mar. 24, 2017 (KR) .................. 10-2017-0037935

(51) Int. Cl.
  *A61K 36/46* (2006.01)
  *A61K 45/06* (2006.01)
  *A61P 1/02* (2006.01)

(52) U.S. Cl.
  CPC .............. *A61K 36/46* (2013.01); *A61K 45/06* (2013.01); *A61P 1/02* (2018.01); *A61K 2300/00* (2013.01)

(58) Field of Classification Search
  None
  See application file for complete search history.

(56) References Cited

U.S. PATENT DOCUMENTS

| | | | | |
|---|---|---|---|---|
| 7,524,518 B2 * | 4/2009 | Kim | .............. | A61K 36/46 424/725 |
| 2007/0275104 A1 * | 11/2007 | Kornman | .............. | A61K 8/97 424/729 |
| 2015/0157553 A1 * | 6/2015 | Ayoola | .............. | A61K 8/97 424/401 |

OTHER PUBLICATIONS

Williams, R., "Periodontal Disease", N Engl J Med 1990; 322:373-382, Feb. 8, 1990.
Salley, K., et al.; "Alveolar bone destruction in the immunosuppressed rat", http://onlinelibrary.wiley.com/doi/10.1111/j.1600-0765.1982.tb01153.x/abstract, 1982.
Listgarten, M.; "Nature of periodontal diseases: Pathogenic mechanisms", Journal of Periodontal Research, 1987, 22, pp. 172-178.
Lohinai, Z., et al.; "Protective effects of mercaptoethylguanidine, a selective inhibitor of inducible nitric oxide synthase, in ligature-induced periodontitis in the rat" Br J Pharmacol Apr. 1998;123(8):741.
Kim, H., "Regulation and implications of inflammatory lymphangiogenesis", Jul. 2012;33(7):350-6. doi: 10.1016/j.it.2012.03.006. Epub May 12, 2012.
Lee, G., et al.; "Aroma-Active Components of *Lycii fructus* (kukija)", Journal of Food Sciences, Jul. 15, 2008.
Hsieh, C., et al.; "Antioxidant actions of Du-zhong (*Eucommia ulmoides* oliv.) toward oxidative damage in biomolecules", Life Sciences, vol. 66, Issue 15, Mar. 3, 2000, pp. 1387-1400.
Lee, DW.; "Periodontitis and dental implant loss", Evid Based Dent. Jun. 2014;15(2):59-60.
Kang D., "Gut microbiota drive the development of neuroinflammatory response in cirrhosis in mice", Hepatology. Oct. 2016;64(4):1232-48.

* cited by examiner

*Primary Examiner* — Susan Hoffman
(74) *Attorney, Agent, or Firm* — Harness, Dickey & Pierce, P.L.C.

(57) ABSTRACT

The present invention relates to a method for preventing, improving or treating a periodontal disease, by administering a composition containing a *moringa* extract and a *eucommia* bark extract as active ingredients. More specifically, the complex composition of a *moringa* extract and a *eucommia* bark extract according to the present invention provides a synergistic effect in improvement of a periodontal disease including gingivitis and periodontitis. Especially, it exhibits an effect of directly preventing or improving a periodontal disease through antioxidant, antibacterial or anti-inflammatory effect, improvement of alveolar bone loss and regeneration of alveolar bone, etc. Accordingly, it can be usefully used as a food, a medicine, a quasi-drug, etc.

8 Claims, 5 Drawing Sheets

METHOD FOR IMPROVING GINGIVITIS AND PERIODONTITIS BY ANTIBACTERIAL, ANTIOXIDANT AND ANTI-INFLAMMATORY EFFECTS AND INHIBITION OF ALVEOLAR BONE LOSS OF COMPLEX EXTRACTS OF MORINGA LEAF AND EUCOMMIA BARK

CROSS-REFERENCE TO RELATED APPLICATION

This application claims the benefit of earlier filing date and right of priority to Korean Application No. 10-2017-0037935, filed on Mar. 24, 2017, the contents of which is incorporated by reference herein in its entirety.

FIELD

The present invention relates to a composition for preventing and improving gingivitis and periodontitis. More specifically, it relates to a composition for preventing and improving gingivitis and periodontitis, which contains an active ingredient derived from a natural substance capable of directly treating periodontitis through alleviation of inflammation of a damaged gingival tissue, inhibition of alveolar bone loss and regeneration and regeneration beyond alleviating the symptoms of gingivitis and periodontitis.

BACKGROUND

Periodontal diseases are representative chronic inflammatory diseases [Williams, 1990; Williams and Paquette, 2000]. Gingivitis and the loss of alveolar bone related thereto are known [Sallay et al., 1982; Samejima et al., 1990]. Proliferation of various bacteria and inflammations caused by them are thought as primary causes [Listgarten, 1987]. Recently, as it is known that the oxidative stress by nitric oxide can cause the diseases [Lohinai et al., 1998], anti-inflammatory, antioxidant and anti-osteoporosis drugs are known to exhibit relatively good results in the prevention and treatment of the periodontal diseases [Kim et al., 2012; Lee et al., 2014; Park et al., 2016; Cheenpracha et al., 2010; Das et al., 2015].

At present, although functional foods or ingredients thereof with adequate compositions are known to have medicinal effects [Lee et al., 2008; Choi et al., 2014ab; Choi et al., 2015; Kang et al., 2015], the effect of improving gingivitis and periodontitis of complex extracts of *moringa* leaf and *eucommia* bark has never been studied.

SUMMARY

The present invention is directed to providing a composition for preventing, improving or treating a periodontal disease including gingivitis and periodontitis, which contains a natural substance as an active ingredient. Particularly, the present invention aims at developing a food composition and a pharmaceutical composition for preventing, improving or treating a periodontal disease, which has an effect of regenerating damaged gingival tissues or directly treating alveolar bone loss beyond alleviating the symptoms of a periodontal disease.

The present invention provides a composition for preventing, improving or treating a periodontal disease, which contains a *moringa* extract and a *eucommia* bark extract as active ingredients, a method for preparing the same and a use thereof.

More specifically, in an exemplary embodiment, there are provided a composition wherein the *moringa* extract is a *moringa* leaf extract and the *eucommia* bark extract is a *eucommia* bark extract, a method for preparing the same and a use thereof.

More specifically, in an exemplary embodiment, the present invention provides a composition wherein an extraction solvent of the *moringa* extract and the *eucommia* bark extract is water, a $C_1$-$C_4$ lower alcohol or a mixture thereof, a method for preparing the same and a use thereof.

More specifically, in an exemplary embodiment, the present invention provides a composition wherein a weight ratio of the *moringa* extract and the *eucommia* bark extract is 1:1 to 8:1 or 8:1 to 2:1 (*moringa* extract:*eucommia* bark extract), a method for preparing the same and a use thereof.

More specifically, in an exemplary embodiment, the present invention provides a composition wherein an extraction solvent of the *moringa* leaf extract or the *eucommia* bark extract is water, a $C_1$-$C_4$ alcohol or a mixture thereof, a method for preparing the same and a use thereof.

In another exemplary embodiment, the present invention provides a composition wherein the periodontal disease is gingivitis or periodontitis, a method for preparing the same and a use thereof.

In another exemplary embodiment, the present invention provides a composition for preventing or improving gingivitis and periodontitis, which is a food composition or a pharmaceutical composition, a method for preparing the same and a use thereof.

In another exemplary embodiment, the present invention provides a composition which further contains one or more extract selected from a group consisting of pomegranate, balloon flower root, *gardeniae* fructus, scutellariae radix, lotus leaf, Chinese mulberry leaf, ginger, peony root, achyranthis radix, red clover, dandelion and dandelion root extracts as an active ingredient, a method for preparing the same and a use thereof.

More specifically, in another exemplary embodiment, the present invention provides a composition wherein the pomegranate extract contains 0.5-3 mg/g of ellagic acid, a method for preparing the same and a use thereof.

More specifically, in another exemplary embodiment, the present invention provides a composition wherein an extraction solvent of the balloon flower root, *gardeniae* fructus, scutellariae radix, lotus leaf, Chinese mulberry leaf, ginger, peony root, achyranthis radix, red clover, dandelion and dandelion root extracts is water, a $C_1$-$C_4$ lower alcohol or a mixture thereof, a method for preparing the same and a use thereof.

Hereunder is given a more detailed description.

The inventors of the present invention have investigated the efficacy of various natural substances safe for human of improving periodontal diseases. In doing so, they have identified that use of a *moringa* extract and a *eucommia* bark extract together provides a significant synergistic effect in improving periodontal diseases. Especially, an effect of regenerating damaged gingival tissues or directly treating alveolar bone loss has been identified beyond alleviating the symptoms of a periodontal diseases.

[Extracts]

The composition according to the present invention contains a *moringa* extract and a *eucommia* bark extract as active ingredients.

Additionally, the composition according to the present invention optionally contains one or more extract selected from a group consisting of pomegranate, balloon flower root, *gardeniae* fructus, scutellariae radix, lotus leaf, Chinese mulberry leaf, ginger, peony root, achyranthis radix, red clover, dandelion and dandelion root extracts as active ingredients. The pomegranate extract refers to a pomegranate concentrate.

*Moringa* is a small tree native to India. But, it is cultivated throughout the world and grows wildly in the regions where the *moringa* is used widely. The family Moringaceae contains 13 species. The most widely known species is *Moringa oleifera*. *Moringa oleifera* is an umbrella-shaped shrub with a height of 4-8 meters. It has 30-70 cm long deciduous leaves. Flowers are white and fragrant and triangular, long green fruits (pods) are 30-40 cm long. It is a multipurpose tree which grows wildly in the foothills of Himalayas in northwestern India and cultivated throughout the tropics. *Moringa* (*Moringa oleifera*) is known to have high nutritional values due to high protein and vitamin contents and various pharmacological activities including antihyperglycemic, anti-inflammatory and anticancer activities. It is known that phytochemicals such as vitamins, flavonoids, amino acids, etc. are abundant in the flower, root, seed, leaf and fruit of *moringa* as compared to other plants. Among the various parts of *moringa*, the leaf is used for antioxidant purposes because it is rich in β-carotene, proteins, vitamin C, calcium, etc. and is reported to be effective in skin inflammations or skin wounds. In addition, the *moringa* leaf is reported to be effective in protecting the liver function, inducing the apoptosis and inhibiting the proliferation of cancer cells, or the like. Specifically, the *moringa* leaf is used in the present invention.

*Eucommia* bark refers to the stem bark of *eucommia* tree (*Eucommia ulmoides* Oliver (family Eucommiaceae)) with the periderm removed. It is board-shaped and the edge portions are somewhat curved inwardly. The length and width are not uniform and the thickness is 3-7 mm. The outer surface is light brown or gray-brown. Some have distinct wrinkle patterns or vertically split patterns and some are relatively thin. Distinct lenticels are observed when the coarse bark is unscraped. The inner surface is smooth and brown or dark brown and has vertical wrinkles. The surface is weak and breaks easily. When it is broken, fine, dense, silvery and elastic rubber threads appear. When the cross section is observed under a microscope, the thick rhytidome is located at the outermost side. Inside the rhytidome, several layers of cork cells are aligned regularly. The cell walls of these cells are lignified and the phelloderm lies therebelow. The phloem takes up most of the area with stone cell rings in a transverse arrangement of 5-7 rows, each ring with 3-5 stone cells. The medullary rays consist of 2-3 rows of cells, located close to the cork layer, sometimes leaning to one side. Parenchyma cells including white gutta-percha can be observed near the pith. These parenchyma cells are particularly abundant inside the phloem. *Eucommia* bark has been used as a representative herbal medicine for hypertension, viral infections, kidney diseases and liver diseases [Hsieh and Yen, 2000; Kwan et al., 2003; Zhao et al., 2008].

Balloon flower root is the root of balloon flower (*Platycodon grandiflorum* A. De Candolle, family Campanulaceae), with the periderm removed or unremoved. It has a thin, long fusiform or conical shape and is often branched. The main root is 10-15 cm in length and 1-3 cm in diameter. The external surface is grayish brown, pale brown or white. The upper end of the root has dented scars of removed stems. The neighborhood of the root has fine lateral wrinkles and longitudinal furrows. The greater part of the root, except the crown, is covered with coarse longitudinal wrinkles, lateral furrows and lenticel-like lateral lines. The texture is hard but easy to break. The transverse section is not fibrous. The cortex is slightly thinner than the xylem, almost white with scattered cracks. The xylem is white to pale brown and the tissue is slightly denser than the cortex. The phloem is wide, the phloem rays on the outside are bent and the phloem bundles are mostly compressed and degenerated. The lactiferous tubes are scattered in bundles and contain a yellow-brown granular substance. Bundles of lactiferous tubes are arranged in the inside phloem along with sieve tubes. The cambium forms a ring. The xylem has wide medullary rays and polygonal vessels, solitary or gathered together in a radiating arrangement.

*Gardeniae* fructus is the well ripe fruit of *Gardenia jasminoides* Ellis (family Rubiaceae) or the fruit passed through hot water. According to a document, *gardeniae* (*Gardenia jasminoides* Ellis) is called mountain *gardeniae* and Korean *gardeniae* (*Gardenia jasminoides* Ellis var. *grandiflora* Nakai) is called big *gardenia* or aqua *gardenia*. However, the Nomenclature of Korean Plants regards the two as the same species. *Gardeniae* is distributed in Japan, Taiwan and China and its fruit is known to have fever-alleviating, choleretic and hemostatic activities.

Scutellariae radix is the root of *Scutellaria baicalensis* Georgi (family Labiatae), with or without the periderm removed. The conical root is twisted and curved. The external surface is yellow-brown to deep yellow. The texture is hard but brittle and easy to cut. The cut surface yellow and the middle part is red-brown. Scutellariae radix is odorless and tastes slightly bitter. It is known to have antibacterial, anti-inflammatory, hypotensive, hemostatic, liver-treating, fever-alleviating, antiemetic and diuretic activities. Major chemical ingredients include forsythol, sterol compounds, saponins, oleanolic acid, etc.

Lotus leaf is the leaf of lotus (*Nelumbo nucifera*). The leaf and flower of lotus emerge respectively from the long leafstalk and the long flower stalk arising from the rhizome and float on top of the water surface. The leaf arises from the rhizome and hangs on the tip of the leafstalk which has grown to a height of 1-2 m. It is around 40 cm in diameter and does not get wet with water. The veins diverge radially and the edge is flat. The leafstalk is thorny and the holes inside communicate with those of the subterranean stem. Because fine hairs invisible to the naked eye are densely packed on the surface of the leaf, water drops roll on the leaf and it does not get wet. The lotus leaf is effective in defeating heat and moisture, stopping bleeding and relieving thrombosis. Therefore, it stops diarrhea caused by heat and moisture, quenches thirst, treats dizziness by clearing the wind-heat of the head and eyes and is helpful in treating various types of hemorrhage, such as hemoptysis, nosebleed, hematuria, metrorrhagia, etc. The lotus leaf is also known to have antibacterial and hypotensive activities, strengthen the stomach and be helpful in beauty care and vigor.

The leaf of Chinese mulberry (*Cudrania tricuspidata* Bureau) is about 6-10 cm in length and grows in alteration from the branch. The leaf has a pointed or blunt oval shape. The edge is often divided into 2 or 3 parts and is not saw-toothed. The leaf of the tree growing between rocks or on hills is small and has a distinctly split edge and a long tail. The leaf is thick. The front side and the leafstalk have fine hairs. The back side has piles. The leaf turns yellow in autumn.

Ginger (*Zingiber officinale*) is a perennial plant in the family Zingiberaceae, order Zingiberales. It is native to Southeast Asia and is cultivated as a vegetable. The rhizome grows sideways. It is fleshy, lumpy and yellow, tastes pungent and smells fragrant. A fake stem made of sheaths stands upright from each node of the rhizome. Its height reaches 30-50 cm and leaves are arranged in two rows in the upper part. The leaves growing in alternation are lancet-shaped, with small widths and long sheaths at the bottom. Flowers do not bloom in Korea. But, in the tropical regions, 20-25 cm long flower stalks surrounded in sheaths come out in August and flowers bloom from the flower buds at the tips thereof. The flower comes from between bracts and is 4-7.6 cm in length. The sepal is barrel-shaped. The end of the corolla diverges into three parts and each split part has a pointed tip. The flower has one stamen and the anther is yellow. It has an inferior ovary and the style is thin like threads.

Peony root refers to root of peony (*Paeonia lactiflora* Pallas) or other plants of the genus *Paeonia* (family Paeoniaceae). It is cylindrical, sometimes curved, 5-20 cm in length and 10-25 mm in diameter. The large root is cut lengthwise. The external surface is white or brown, with distinct longitudinal wrinkles, often with wrinkles or scars of lateral roots and with laterally elongated lenticels. The upper part of the root often has scars of the stem or unremoved brown cortex. The texture is hard and difficult to fracture. The transverse section is granular and very dense. Under a magnifying glass, the cambium is distinct, milky white or brown, and a radial path is observed.

Achyranthis radix is the root of *Achyranthes japonica* Nakai or *Achyranthes bidentata* Blume (family Amaranthaceae). It is a cylindrical main root with numerous lateral roots, 5-20 cm in length and 3-5 mm in diameter, with short remains of the rhizome at the top. The external surface is grayish yellow to pale yellow. The texture is hard and brittle and the fractured surface is horn-like, yellowish white to yellowish brown.

Red clover (*Trifolium pratense* L) is a perennial grass in the family Fabaceae. It has many other names including *trifolium*. It is native to the shores of the Mediterranean Sea and Southwest Asia and is widely distributed and cultivated throughout the world. Red clover is used as a fodder and the young leaves are often eaten as a vegetable after being slightly dipped in boiling water in spring. Red clover is known to be effective in treating cough or asthma due to its expectorant effect. It can be divided into the aerial part and the root part. Specifically, the aerial part is used in the present invention.

Dandelion (*Taraxacum platycarpum*) is a plant belonging to the class Dicotyledoneae of the phylum Angiospermae and grows on the sunny side of the field. It has no stem and the leaves grow in clusters from the root and spread sideways. The leaf has a shape of an inverted lancet, is 6-15 cm in length and 1.2-5 cm in width. It has deep indentations like feather and is saw-toothed and slightly hairy at the edge.

The root of dandelion is 7-8.5 mm in length and the pappus is 6 mm in length and is pale white.

In the present invention, the term "extract" includes an extract obtained from extraction and extracts of all forms that can be obtained from the extract, including a diluted or concentrated solution of the extract, a dried product obtained by drying the extract, a crude purification product or a purification product of the extract, a mixture thereof, etc.

Within a range not negatively affecting the purpose of the present invention, the extract according to the present invention may contain, in addition to the specified part of each plant, its leaf, stem, bark, root, flower, flower bud, fruit, seed, sap and whole plant.

The extract according to the present invention may be prepared by those of ordinary skill using any appropriate method known in the art. For example, it may be prepared by solvent extraction. A solvent extract may be obtained by pulverizing the whole plant or any part of it (e.g., using a blender) and then treating with an extraction solvent. A drying process may precede the pulverization. Also, the solvent extract may be prepared into a powder through an addition process such as distillation under reduced pressure, freeze-drying, spray drying, etc.

The extraction solvent is not particularly limited any solvent known in the art may be used. Non-limiting examples of the extraction solvent include: water; a $C_1$-$C_4$ lower alcohol such as methanol, ethanol, propyl alcohol, butyl alcohol, etc.; a polyhydric alcohol such as glycerin, butylene glycol, propylene glycol, etc.; a hydrocarbon-based solvent such as methyl acetate, ethyl acetate, acetone, benzene, hexane, diethyl ether, dichloromethane, etc.; or a mixture thereof. Specifically, water or a $C_1$-$C_4$ lower alcohol may be used either alone or in combination. A solvent extract may be prepared by conducting extraction one or more times using the solvent and the solvent extract may be prepared into a dried extract by conducting distillation under reduced pressure and then freeze-drying or spray-drying the same.

The amount of the extraction solvent may vary depending on the extraction solvent used. For example, it may be used in an amount of 1-20 times or 5-20 times, more specifically 5-10 times, most specifically 5-8 times, based on the dry weight of the corresponding plant.

The solvent extraction may be performed at a 100-150° C. and 0.1-0.3 MPa for 5-10 hours, although not being limited thereto.

In addition, various extraction processes known in the art, e.g., maceration, infusion, percolation, digestion, decoction, hot continuous extraction, aqueous-alcoholic extraction, countercurrent extraction, microwave-assisted extraction, ultrasonic extraction, supercritical fluid extraction, phytonic extraction (e.g., using a hydrofluorocarbon solvent), etc. may be used either alone or in combination.

The red clover extract according to the present invention may contain 50-400 mg/g of isoflavones based on the total red clover extract. It is thought that the reason why the red clover extract according to the present invention may contain isoflavones of the above-described concentration is because of the difference in region, used part, preparation method (e.g., extraction solvent), etc. However, the present invention is not limited thereby.

The *eucommia* bark extract according to the present invention may contain 1.0-15 mg/g of pinoresinol diglucoside based on the total *eucommia* bark extract. It is thought that the reason why the *eucommia* bark extract according to the present invention may contain pinoresinol diglucoside of the above-described concentration is because of the difference in region, used part, preparation method (e.g., extraction solvent), etc. However, the present invention is not limited thereby.

The *moringa* extract according to the present invention may contain 1.2-5 mg/g of astragalin based on the total *moringa* extract. It is thought that the reason why the *moringa* extract according to the present invention may contain astragalin of the above-described concentration is because of the difference in region, used part, preparation method (e.g., extraction solvent), etc. However, the present invention is not limited thereby.

Pomegranate (*Punica granatum* L) is a plant native to southwestern Asia, northwestern India and California of the USA and is widely distributed in subtropical and tropical regions at present. From long ago, pomegranate, especially red pomegranate, has been known as a tonic. In particular, it is known to have good effects on prevention of hypertension and arteriosclerosis. It contains water-soluble sugars in large quantities of 38-47% and also contains various vitamins and minerals.

Specifically, the pomegranate used in the present invention may be red pomegranate, although not being specially limited thereto. Specifically, red pomegranate from Iran, California, Taiwan, Uzbekistan, Turkey or Korea may be used. For example, Turkish pomegranate cultivars include Hicaznar pomegranate cv., Cekirdeksiz VI pomegranate cv., Silifke Asisi pomegranate cv., Katirbasi pomegranate cv., Lefan pomegranate cv., etc., although not being limited thereto. The pomegranate extract according to the present invention may vary depending on the region, harvest time, etc. of the pomegranate.

In the present invention, the term "concentrate" includes a concentrate obtained by the method described below and concentrates of all forms that can be obtained from the concentrate, including a diluted solution of the concentrate, a dried product obtained by drying the concentrate, a crude purification product or a purification product of the concentrate, a mixture thereof, etc.

Specifically, pomegranate pulp may be used to prepare the pomegranate concentrate according to the present invention.

The pomegranate concentrate according to the present invention may be prepared as follows. For example, after washing pomegranate, the rind and seeds are completely removed. After sterilizing at high temperature in a short time, polysaccharides such as starch contained in the pomegranate are degraded by adding a starch-degrading enzyme. Then, after optionally controlling the turbidity, color, viscosity, etc. of the pomegranate concentrate by adding an additive such as gelatin, silicon dioxide, bentonite, silica sol, tannin, cellulose, potassium caseinate, etc., the pomegranate concentrate may be prepared by concentrating under heating. In addition, a filtering step may be included in between the respective steps. For example, one or more filtering step may be included between the step of removing the rind and seeds and the step of sterilizing at high temperature, between the step of treating with the starch-degrading enzyme and the concentration step or after the concentration step.

More specifically, the concentrate may be prepared through the following steps:

S1) a step of removing the rind and seeds of pomegranate and obtaining the pomegranate pulp only;

S2) a step of sterilizing the pomegranate pulp at 100-105° C. for 50-80 seconds and then cooling to 48-55° C.;

S3) a step of treating the cooled pomegranate pulp with a starch-degrading enzyme at 48-55° C.; and S4) a step of concentrating the degraded pomegranate pulp under heating sequentially at high temperature and high pressure of 70-100° C. and 400-850 mbar for two or more times and at low temperature and low pressure of 40-80° C. and 100-350 mbar for one or more time.

Optionally, a filtering step may be included between the step 51 and the step S2, between the step S3 and the step S4 or after the step S4.

Hereinafter, each step is described in more detail.

S1) Removing Rind and Seeds of Pomegranate and Obtaining Pomegranate Pulp Only

The present invention provides an extract using only the pomegranate pulp not containing the rind and seeds of pomegranate. The rind and seeds of pomegranate may cause side effects. For example, pomegranate certain alkaloids contained in the rind may negatively affect the body function and poisoning may cause seizure, convulsion, stupor, etc. by affecting the respiratory system and muscles. And, the extract of pomegranate seeds may cause allergic side effects such as tongue swelling in some people.

S2) Sterilizing Pomegranate Pulp at 100-105° C. for 50-80 Seconds and then Cooling to 48-55° C.

The pomegranate pulp is sterilized and then cooled. The sterilization is performed at 100-105° C. for 50-80 seconds, more specifically quickly for 55-70 seconds, and the cooling is performed specifically at 48-55° C.

S3) Treating Cooled Pomegranate Pulp with Starch-Degrading Enzyme at 48-55° C.

The cooled pomegranate pulp is treated with a starch-degrading enzyme. The treatment may be performed specifically at 48-55° C. for 10-60 minutes, more specifically at 48-55° C. for 20-40 minutes. As the starch-degrading enzyme, various starch-degrading enzymes known in the art may be used without particular limitation. For example, pectinase, proteinase, amylase, cellulase, etc. may be used. Specifically, pectinase may be used.

S4) Concentrating Degraded Pomegranate Pulp Under Heating Sequentially at High Temperature and High Pressure of 70-100° C. and 400-850 Mbar for Two or More Times and at Low Temperature and Low Pressure of 40-80° C. and 100-350 Mbar for One or More Time The degraded pomegranate pulp is concentrated under heating sequentially at high temperature and high pressure and at low temperature and low pressure.

Specifically, it may be concentrated under heating at high temperature and high pressure for two or more times, more specifically three or more times, and may be concentrated under heating at low temperature and low pressure for one or more time, more specifically two or more times, for a total of three or more times.

The concentration under heating at high temperature and high pressure is performed at 70-100° C. and 400-850 mbar. Within the above temperature and pressure ranges, the temperature and pressure may be varied for each run of the concentration under heating without limitation. Specifically, the concentration under heating may be performed firstly at 70-85° C. and 400-550 mbar, secondly at 85-92° C. and 550-750 mbar and thirdly at 92-100° C. and 750-850 mbar. More specifically, the concentration under heating may be performed firstly at 78-82° C. and 450-500 mbar, secondly at 85-90° C. and 600-650 mbar and thirdly at 92-98° C. and 800-850 mbar.

The concentration under heating at low temperature and low pressure is performed at 40-80° C. and 100-350 mbar. Within the above temperature and pressure ranges, the temperature and pressure may be varied for each run of the concentration under heating without limitation. Specifically, the concentration under heating may be performed fourthly at 60-80° C. and 250-350 mbar and fifthly at 40-60° C. and 100-250 mbar. More specifically, the concentration under heating may be performed fourthly at 65-72° C. and 300-330 mbar and fifthly at 45-55° C. and 100-150 mbar.

The pomegranate concentrate according to the present invention contains 0.5-3 mg/g of ellagic acid based on the total weight of the pomegranate concentrate. It is thought that the reason why the pomegranate concentrate according to the present invention contains ellagic acid at the high content is because of the difference in region, use of the pulp only, preparation method (e.g., concentration method, heating temperature and pressure), etc. However, the present invention is not limited thereby.

[Compositions]

The present invention provides a composition for use in preventing, improving or treating a periodontal disease. More specifically, the present invention provides a composition for use in preventing, improving or treating a periodontal disease, which contains a *moringa* extract and a *eucommia* bark extract as active ingredients.

The composition according to the present invention contains a *moringa* extract and a *eucommia* bark extract as active ingredients.

In addition, the composition according to the present invention optionally contains one or more extract selected from a group consisting of pomegranate, balloon flower root, *gardeniae* fructus, scutellariae radix, lotus leaf, Chinese mulberry leaf, ginger, peony root, achyranthis radix, red clover, dandelion and dandelion root extracts as an active ingredient.

In the present invention, "contains as an active ingredient" means addition in an amount capable of exhibiting the effect of preventing, improving or treating a periodontal disease with the composition according to the present invention. In addition, various adjuvant ingredients for delivery to target cells, stabilization, etc. may be added for formulation into various forms.

In the composition according to the present invention, the respective ingredients may be contained at the following ratios.

A weight ratio of the *moringa* extract and the *eucommia* bark extract may be 1:1-8:1 or 8:1-2:1 (*moringa* extract: *eucommia* bark extract). More specifically, the weight ratio of the *moringa* extract and the *eucommia* bark extract may be 2:1-4:1 (*moringa* extract: *eucommia* bark extract). A superior synergistic effect is achieved within the above weight ratio ranges.

In addition, each extract (and concentrate) of the composition according to the present invention may be contained in the final composition within a range of about 0.0001-90%, 0.001-90%, 0.01-90%, 0.1-90%, 0.1-90%, 0.1-80%, 0.1-70%, 0.1-60%, 0.1-50%, 0.1-40%, 0.1-30%, 0.1-20% or 0.1-10%.

Also, the composition according to the present invention may contain the complex of the present invention within a range of about 0.0001%, 0.001%, 0.01%, 0.1%, 1%, 5%, 10%, 15%, 20%, 25%, 30%, 35%, 40%, 45%, 50%, 60%, 65%, 70%, 75%, 80%, 85%, 90% or 99% or higher.

The % may be calculated as weight based on the total weight or volume based on the total volume of the composition and the concentration may be controlled depending on the desired effect of the composition or the product in which the composition is used.

The composition according to the present invention may be prepared by mixing a *moringa* extract and a *eucommia* bark extract prepared by the method described above. In addition, it may be prepared by optionally mixing with one or more extract selected from a group consisting of pomegranate, balloon flower root, *gardeniae* fructus, scutellariae radix, lotus leaf, Chinese mulberry leaf, ginger, peony root, achyranthis radix, red clover, dandelion and dandelion root extracts prepared by the method described above. In addition, an additional process may be introduced to improve the storage, distribution and stability properties of the composition.

The composition according to the present invention may be prepared into various products. For example, it may be prepared into a food composition, a pharmaceutical composition, an oral product, etc.

The present invention provides a pharmaceutical composition containing one of the compositions described above. The present invention provides a method for preventing, improving or treating a periodontal disease by administering one of the compositions described above.

The pharmaceutical composition according to the present invention may contain a pharmaceutically effective amount of the *moringa* extract and the *eucommia* bark extract alone and, optionally, one or more extract selected from a group consisting of pomegranate, balloon flower root, *gardeniae* fructus, scutellariae radix, lotus leaf, Chinese mulberry leaf, ginger, peony root, achyranthis radix, red clover, dandelion and dandelion root extracts. In addition, it may further contain one or more pharmaceutically acceptable carrier, excipient or diluent.

The term "pharmaceutically acceptable" means a nontoxic composition which is physiologically acceptable and, when administered to a human, generally does not cause allergic reactions such as gastrointestinal disorder and dizziness or reactions similar thereto while not negatively affecting the action of the active ingredients.

Examples of the carrier, excipient or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, mineral oil, etc. In addition, the pharmaceutical composition may further contain a filler, an anticoagulant, a lubricant, a wetting agent, a fragrance, an emulsifier, an antiseptic, etc.

The "pharmaceutically effective amount" refers to an amount exhibiting a desired effect as compared to a negative control group, specifically an amount sufficient to improve, prevent and/or treat a periodontal disease.

In addition, the pharmaceutical composition of the present invention may be prepared into a formulation that can provide fast, continued or delayed release of the active ingredient after being administered to a mammal using the method known in the art. The formulation may be a powder, a granule, a tablet, an emulsion, a syrup, an aerosol, a soft or hard gelatin capsule, a sterile injection solution or a sterilized powder.

The pharmaceutical composition of the present invention may be administered orally or parenterally although the administration route is not limited thereto. Examples of parenteral administration routes may include transdermal, intranasal, intraabdominal, intramuscular, subcutaneous or intravenous routes. For oral administration, the composition may be formulated as a tablet, a capsule, a cachet, a gelcap, a solution, a suspension, etc. The tablet or capsule may be prepared by a commonly employed method together with a pharmaceutically acceptable excipient such as a binder (e.g., pregelatinized cornstarch, polyvinylpyrrolidone or hydropxypropyl methyl cellulose), a filler (e.g., lactose, microcrystalline cellulose or calcium hydrogen phosphate), a lubricant (e.g., magnesium stearate, talc or silica), a disintegrant (e.g., potato starch or sodium starch glycolate) or a wetting agent (e.g., sodium lauryl sulfate). The tablet may be coated according to a method well known in the art. A liquid formulation for oral administration may be a solution, a syrup or a suspension, although not being limited thereto. Before being used, it may exist as an anhydrous form to be mixed with water or another suitable vehicle. The liquid formulation may be prepared by a commonly employed method using a pharmaceutically acceptable additive such as a suspending agent (e.g., sorbitol syrup, cellulose derivative or hydrogenated edible fat), an emulsifier (e.g., lecithin or acacia gum), a nonaqueous vehicle (e.g., almond oil, oily ester, ethyl alcohol or fractionated vegetable oil) or an antiseptic (e.g., methyl or propyl p-hydroxybenzoate or sorbic acid). The formulation may contain a buffering salt, a flavor, a colorant or a sweetener as occasion demands. The formulation for oral administration may be prepared to provide slow, controlled or continued release of the active ingredient to treat a periodontal disease.

A preferred administration dosage of the composition of the present invention may be adequately determined by those skilled in the art although it varies depending on the condition and body weight of a patient, degree of a disease, composition type, administration route and administration period.

The composition of the present invention may be used either alone or in combination with surgery, radiation therapy, hormone therapy, chemotherapy or a method using a biological response modifier. For example, the pharmaceutical composition of the present invention may be administered or in combination with a compound known to have an effect of improving, preventing and/or treating a periodontal disease.

The present invention provides a food composition containing the composition. The present invention also provides a method for preventing or improving a periodontal disease by administering the composition.

The food composition according to the present invention may contain a sitologically effective amount of a *moringa* extract and a *eucommia* bark extract alone or may further contain one or more sitologically acceptable carrier, excipient or diluent.

The food composition of the present invention includes all types of processed natural substances, including a food, a functional food, a nutritional supplement, a health food, a food additive, etc. The food composition may be prepared into various forms according to common methods known in the art.

The type of food is not particularly limited. Examples of the food to which the active ingredient can be added include a drink, a meat, a sausage, a bread, a biscuit, a rice cake, a chocolate, a candy, a snack, a cookie, a pizza, an instant noodle, other noodles, a gum, a dairy product including ice cream, a soup, a beverage, an alcohol beverage, a vitamin complex, a milk product, a processed milk product and common health foods.

The complex of the *moringa* extract and the *eucommia* bark extract according to the present invention may be added to a food either alone or in combination with another food or a food ingredient and may be used adequately according to a common method. The mixing amount of the active ingredient may be determined appropriately depending on the purpose of use (for prevention or improvement). Generally, the amount of the complex in a health food may be 0.1-90 wt % based on the total weight of the food. However, the amount may be smaller when it is ingested for a long period of time for the purpose of health or hygiene. In addition, the active ingredient may be used in a larger amount than the above-described range because it has no safety problem.

The food composition of the present invention may contain, in addition to the complex of the *moringa* extract and the *eucommia* bark extract of the specified ratio as an essential ingredient, other ingredients without particular limitation. It may contain optionally one or more extract selected from a group consisting of pomegranate, balloon flower root, *gardeniae* fructus, scutellariae radix, lotus leaf, Chinese mulberry leaf, ginger, peony root, achyranthis radix, red clover, dandelion and dandelion root extracts and may further contain various flavors, natural carbohydrates, etc. commonly used in drinks. Examples of the natural carbohydrate include a sugar such as a monosaccharide, e.g., glucose, fructose, etc., a disaccharide, e.g., maltose, sucrose, etc. and a polysaccharide, e.g., dextrin, cyclodextrin, etc. and a sugar alcohol such as xylitol, sorbitol, erythritol, etc. In addition, a natural flavor (thaumatin or *stevia* extract (e.g., rebaudioside A, glycyrrhizin, etc.)) or a synthetic flavor (saccharin, aspartame, etc.) may be advantageously used as a flavor.

In addition, the food composition of the present invention may contain various nutrients, vitamins, minerals (electrolytes), flavors such as synthetic flavors and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated beverages, etc. In addition, it may contain a pulp for preparing a natural fruit juice, a fruit juice drink or a vegetable drink.

In addition, the present invention provides an oral product containing the composition. The oral product is effective in preventing or improving a periodontal disease. The oral product may be a toothpaste, a mouth rinse, an oral spray, a gum, an ointment, a patch, etc.

The oral product may further contain an adequate amount of a commonly used additive selected from a group consisting of an abrasive, a humectant, a binder, a foaming agent, a sweetener, an antiseptic, a remedial agent, a flavor, an acidity-controlling agent, a whitening agent, etc. depending on the type and purpose of use.

For example, the abrasive may be one or more selected from a group consisting of dicalcium phosphate, precipitated silica, calcium carbonate, hydrated alumina, kaolin, sodium bicarbonate ($NaHCO_3$), etc. The humectant may be one or more selected from a group consisting of glycerin, sorbitol, non-crystalline sorbitol, propylene glycol, polyethylene glycol, xylitol, etc., although not being limited thereto. The binder may be one or more selected from a group consisting of carrageenan, xanthan gum, sodium carboxymethyl cellulose, carboxyvinyl polymer, sodium alginate, laponite, etc., although not being limited thereto. The foaming agent may include one or more selected from a group of an anionic surfactant such as sodium lauryl sulfate, sodium lauroyl sarcosinate, etc., a condensed polymer such as sorbitan fatty add ester, polyoxyethylene hydrogenated castor oil, polyoxyethylene, polyoxypropylene, etc., although not being limited thereto. The sweetener may include one or more than two selected from a group of sodium saccharin, aspartame, glycyrrhizinic acid etc., although not being limited thereto. The antiseptic may include one or more selected from a group of p-oxybenzoic acid ester, sodium benzoate, etc. The remedial agent may be sodium fluoride, sodium fluorophosphate, tin fluoride, amine fluoride, chlorhexidine, tranexamic acid, allantoin, caproic acid, polyphosphate, an enzyme, an herbal extract, etc. The flavor may be peppermint oil, spearmint oil, menthol, carvone, etc. mixed in appropriate ratios. The acidity-controlling agent may be phosphoric acid, sodium phosphate, citric acid, sodium citrate, succinic acid, sodium succinate, tartaric acid, sodium tartrate, etc. and the preferred acidity is about 5-8. The whitening agent may be titanic oxide, although not being limited thereto.

The composition according to the present invention may be provided as a kit.

The composition according to the present invention is contained in a container. The container may include a bottle, a metal tube, a laminate tube, a plastic tube, a dispenser, a pressurized container, a barrier container, a package, a compartment, a compact container, a pan that can hold a composition, or other types of containers such as a plastic container injection- or blow-molded into a bottle, dispenser or package in which a dispersion medium or a composition is retained, although not being limited thereto. The kit may contain an instruction about the use of the kit or the composition. The instruction may be described in a separate paper or may be described on the surface of the container or on the surface of a packaging material of the container. The instruction may include a word, a phrase, an abbreviation, a picture, a symbol, etc., although not being limited thereto. For example, the instruction may include instructions about how to use, apply or maintain the kit or the composition. The container may contain a predetermined amount of the composition.

[Improvement, Prevention and/or Treatment of Periodontal Disease]

The composition according to the present invention is effective in improving, preventing and/or treating a periodontal disease.

More specifically, the composition according to the present invention has an effect of alleviating and improving the symptoms of a periodontal disease and, furthermore, directly treating damage to the gingiva and the periodontium through wound healing, anti-inflammation and inhibition of alveolar bone loss and regeneration thereof.

The periodontal disease may be one or more disease selected from a group consisting of stomatitis, gingivitis, periodontitis, alveolar bone breakage, alveolar bone osteoporosis, alveolar bone osteomalacia, alveolar bone osteopenia, alveolar bone osteodystrophy, etc. Specifically, it may be gingivitis or periodontitis.

The composition according to the present invention is safe for the human body because it contains natural substances as active ingredients. Especially, it has an effect of treating damage from gingiva and periodontium directly through wound healing, anti-inflammation and inhibition of alveolar bone loss and regeneration thereof beyond alleviating the symptoms of gingivitis and periodontitis. Accordingly, it can be usefully used as a composition for preventing, improving or treating a periodontal disease including gingivitis and periodontitis in various applications (food, medicine, quasi-drugs, etc.).

BRIEF DESCRIPTION OF THE DRAWINGS

The accompanying drawings illustrate a preferred embodiment of the present invention and together with the foregoing disclosure, serve to provide further understanding of the technical features of the present invention, and thus, the present invention is not construed as being limited to the drawings.

DETAILED DESCRIPTION

Figure 1:
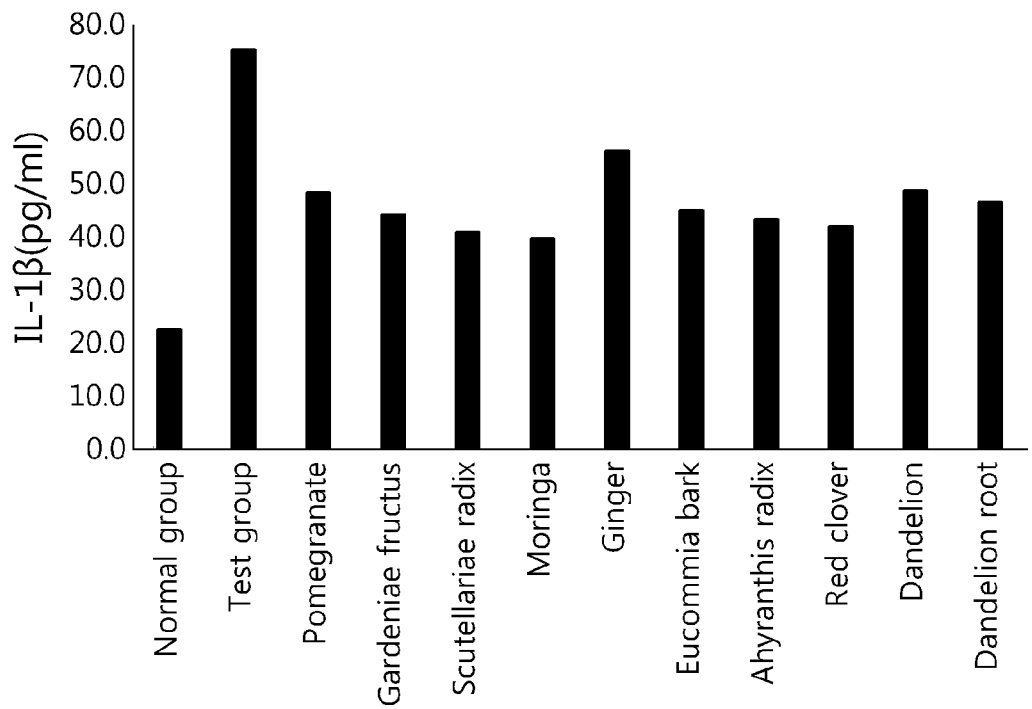
FIG. 1 shows a result of investigating anti-inflammatory effect by treating a gingivitis-induced animal model with 11 natural substances and then measuring the content of IL-1β in the gingival tissue.

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications can be made thereto without departing from the scope of the disclosure.

EXAMPLES

1. Preparation of Test Substances

Extracts of pomegranate, balloon flower root, *gardeniae fructus*, *scutellariae radix*, *moringa*, lotus leaf, Chinese mulberry leaf, ginger, peony root, *achyranthis radix*, *eucommia* bark, red clover, dandelion and dandelion root (i.e., 14 natural substances) were prepared according to the preparation process described below. For each raw material, two or more lots were prepared under the described extraction conditions and extraction yield, contents of ingredients, properties, etc. were analyzed.

1.1 Preparation of Concentrated Pomegranate Powder

A pomegranate concentrate was prepared as follows.

First, 1000 kg of pomegranate were washed after removing foreign materials and sorting out damaged fruits. The separated fruits were cut and the rind and seeds were removed to obtain 450 kg of a pomegranate pulp. After filtration, the pomegranate pulp was sterilized at 100-105° C. for 60 seconds and then cooled to 48-55° C. By adding pectinase 70-100 mL per 1000 L of the resulting pomegranate juice, starches were degraded at 48-55° C. for 30 minutes. Then, after adding 900 g of bentonite per 10000 L of the pomegranate juice to maintain turbidity and color and provide viscosity favorable for drinking, the mixture was stirred at 48-55° C. for 10 minutes. Then, after filtering through 1.5-mm and 1-mm filters under reduced pressure, the mixture was concentrated under heating (sequentially, at 80° C. and 475 mbar to 12 Brix, at 87° C. and 626 mbar to 17 Brix, at 95° C. and 847 mbar to 31 Brix, at 70° C. and 312 mbar to 43 Brix, and at 49° C. and 118 mbar to 65 Brix). Then, a pomegranate concentrate containing 1.8-3.0 mg/g of ellagic acid was obtained by filtering the mixture through a 0.15-mm filter. Finally, a concentrated pomegranate powder containing 0.5-3 mg/g of ellagic acid was prepared by mixing the pomegranate concentrate with dextrin at a ratio of 9:1 and then spray-drying the same.

1.2 Preparation of Extracts of 13 Natural Substances Including *Moringa*

Balloon flower root, *gardeniae* fructus, scutellariae radix, *moringa*, lotus leaf, Chinese mulberry leaf, ginger, peony root, achyranthis radix, *eucommia* bark, dandelion and dandelion root extracts were prepared as follows.

As the *eucommia* bark, dried (roasted) *eucommia* bark was used. As the *moringa, moringa* leaf was used. As the red clover extract, one containing 8% isoflavone was purchased from Biosearch Life Co. Ltd. (Spain).

30 kg of each of the dried raw materials was weighed exactly, washed cleanly and then extracted in an extractor with a raw material:solvent ratio of 3:20 (kg:kg) at 121° C. and 0.15 MPa for 6 hours. This procedure was repeated 2 times. As the solvent, water was used. After removing solid contents by filtering the extract, the filtrate was concentrated under reduced pressure to obtain a concentrate of 25 Brix (±5 Brix). The concentrate was prepared into a powder through spray drying after mixing with a concentrate:dextrin ratio of 9:1 (kg:kg). Each powdered extract was subjected to ingredient analysis for standardization of raw material and preparation process and safety and efficacy were evaluated through in-vivo and in-vitro experiments.

2. Evaluation of Efficacy of 14 Natural Substances

The gingivitis- and periodontitis-improving effect of the concentrated pomegranate powder prepared in 1.1 and the 13 samples prepared in 1.2 was investigated for an EPD model.

2.1. Evaluation of Efficacy Through Animal Experiment

The gingivitis- and periodontitis-improving effect of each of the concentrated pomegranate powder and the 13 extracts containing *moringa* leaf (balloon flower root, *gardeniae* fructus, scutellariae radix, *moringa*, lotus leaf, Chinese mulberry leaf, ginger, peony root, achyranthis radix, *eucommia* bark, red clover, dandelion and dandelion root) was evaluated.

Also, the gingivitis- and periodontitis-improving effect of the *moringa* leaf extract (MF) and the *eucommia* bark extract (EC) alone or in combination was evaluated.

2.1.1 Evaluation of Efficacy of 14 Natural Substance Extracts Through Animal Experiment The gingivitis- and periodontitis-improving effect of each of the concentrated pomegranate powder and the 13 extracts containing *moringa* leaf (balloon flower root, *gardeniae* fructus, scutellariae radix, *moringa*, lotus leaf, Chinese mulberry leaf, ginger, peony root, achyranthis radix, *eucommia* bark, red clover, dandelion and dandelion root) was evaluated.

The gingivitis- and periodontitis-improving effect was evaluated using rats with ligature-induced experimental periodontitis (EPD). 24 hours after the ligature of the cervical portion, each extract dissolved in sterilized distilled water was orally administered at a dosage of 5 mL/kg (200 mg/kg) once a day for 10 days and the change in the amount of interleukin (IL)-1β in the gingival tissue and the alveolar bone volume was observed along with histopathological changes. A group to which 5 mg/kg indomethacin (IND), which is a nonsteroidal anti-inflammatory drug (NSAID), was orally administered was used as a control group.

Composition and Administration of Test Substances

Each of the concentrated pomegranate powder and the 13 extracts containing *moringa* leaf (balloon flower root, *gardeniae* fructus, scutellariae radix, *moringa*, lotus leaf, Chinese mulberry leaf, ginger, peony root, achyranthis radix, *eucommia* bark, red clover, dandelion and dandelion root) was dissolved in sterilized distilled water to a concentration of 40 mg/mL and orally administered at a dosage of 5 mL/kg (200 mg/kg) from 24 hours after the ligature of the cervical portion once a day for 10 days. Also, IND dissolved in sterilized distilled water to a concentration of 1 mg/mL was orally administered at a dosage of 5 mL/kg (5 mg/kg) from 24 hours after the ligature of the cervical portion once a day for 10 days. For a normal control group and an EPD (periodontal disease) control group, only sterilized distilled water was administered instead of the natural substance extract with the same dosage and frequency.

Induction of Periodontal Disease

According to the method previously reported by the inventors of the present invention [Lee et al., 2014; Park et al., 2016], the experimental animals were accustomed to the laboratory environment for 10 days and generally inhalation anesthetized with a mixture gas of 3% isoflurane (Nana Pharm. Co., Hwaseong, Korea), 70% $N_2O$ and 28.5% O2 using an inhaler (Surgivet, Waukesha, Wis., USA) and a ventilator (Model 687, Harvard Apparatus, Cambridge, UK). The cervical portion of the left incisor was ligated with 3-0 nylon suture to induce periodontitis and gingiva. For a normal control group, the cervical portion of the incisor was not ligated.

Investigation of Change in Interleukin (IL)-1β in Gingival Tissue

After EPD for 11 days, the gingival tissue was homogenized and subjected to measurement with the IL-1β rat ELISA kit (Abcam, Cambridge, UK). The experiment was conducted according to the manufacturer's instructions. 100 µL of the homogenized sample and reference standard were added to each well and then incubated in a 37° C. incubator for 2 hours. After removing the supernatant and adding 100 µL of a 1× biotin-conjugated antibody to each well, incubation was conducted in a 37° C. incubator for 1 hour. After removing the supernatant from each well and washing 3 times, 100 µL of 1× horseradish peroxidase-conjugated avidin was added and incubation was conducted at 37° C. for an hour. After adding 90 µL of 3, 3', 5, 5'-tetramethylbenzidine to each well, incubation was conducted at 37° C. for 15-30 minutes. After adding 50 µL of a stop solution to each well, absorbance was measured with a microplate reader (Tecan, Mannedofr, Switzerland) at a wavelength of 450 nm.

Investigation of Change in Alveolar Bone Volume

Alveolar bone loss was measured according to the method of Crawford et al. [1987]. The rat was sacrificed 10 days after the sample administration (11 days after EPD 11) and the teeth and the gingiva were exposed as much as possible. The area between the end of the gingiva and the end of the incisor between the two teeth subjected to EPD was expressed as mm/rat.

2.1.1.1. Investigation of Gingivitis- and Periodontitis-improving Effect Through Change in IL-1β Content in Gingival Tissue in Periodontal Disease-induced Model for 14 Natural Substance Extracts (FIG. 1)

For the EPD control group, the IL-1β in the gingival tissue was significantly increased (p<0.01) as compared to the normal control group. The groups administered with IND and *moringa* leaf, scutellariae radix, red clover, achyranthis radix, *gardeniae* fructus, *eucommia* bark, dandelion root, pomegranate, dandelion, ginger and balloon flower root extracts showed significantly decrease (p<0.01) in the IL-1β content as compared to the EPD control group, in that order. Meanwhile, the groups administered with lotus leaf, Chinese mulberry leaf and peony root extracts did not show significant change in the IL-1β content in the gingival tissue as compared to the EPD control group.

Figure 2:
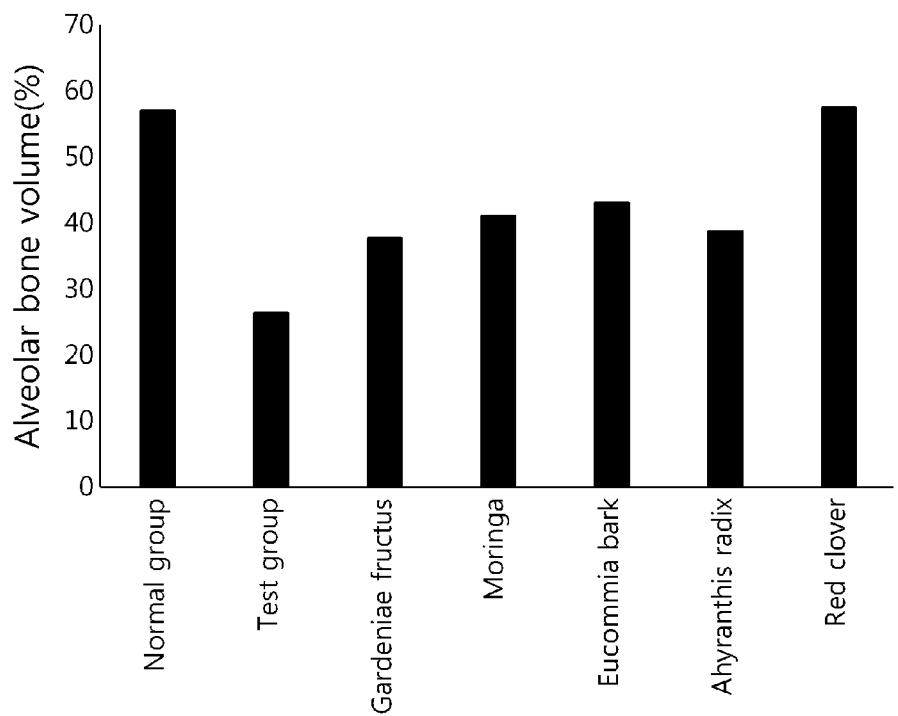
FIG. 2 shows a result of investigating alveolar bone loss-inhibiting effect by treating a periodontitis-induced animal model with 5 natural substances and then measuring alveolar bone volume.

2.1.1.2. Investigation of Gingivitis- and Periodontitis-improving Effect Through Change in Alveolar Bone Volume in Periodontal Disease-induced Model for 14 Natural Substance Extracts (FIG. 2)

For the EPD control group, the alveolar bone volume was significantly decreased (p<0.01) as compared to the normal control group. The groups administered with IND and red clover, *eucommia* bark, *moringa* leaf, achyranthis radix and *gardeniae* fructus extracts showed significantly increase (p<0.01 or p<0.05) in the alveolar bone volume as compared to the EPD control group, in that order. Meanwhile, the groups administered with pomegranate, balloon flower root, scutellariae radix, lotus leaf, Chinese mulberry leaf, ginger, peony root, dandelion and dandelion root did not show significant change in the alveolar bone volume as compared to the EPD control group.

2.1.2 Evaluation of Efficacy of *Moringa* Leaf Extract (MF), *Eucommia* Bark Extract (EC) and Complex Thereof Through Animal Experiment The gingivitis- and periodontitis-improving effect was evaluated using rats with ligature-induced experimental periodontitis (EPD). 9 complex compositions of the *moringa* leaf extract (MF) and the *eucommia* bark extract (EC) (MF:EC=1:1, 1:2, 1:4, 1:6, 1:8, 2:1, 4:1, 6:1 and 8:1; mg:mg) dissolved in sterilized distilled water were orally administered at a dosage of 5 mL/kg (200 mg/kg) once a day for 10 days and body weight, alveolar bone, number of viable aerobic bacteria in the oral tissue, interleukin (IL)-1β and tumor necrosis factor (TNF)-α contents in the gingiva, lipid peroxidation (malondialdehyde (MDA) content) and change in the activity of inducible nitric oxide synthase (iNOS) and myeloperoxidase (MPO) were observed together with histopathological changes. With reference to the previous report [Kang et al., 2016], the complex compositions exhibiting statistically significant (p<0.01 or p<0.05) increase in medicinal effect as compared to the MF and EC compositions alone were regarded as the MF:EC complex compositions exhibiting a synergistic effect. A group to which 5 mg/kg indomethacin (IND), which is a nonsteroidal anti-inflammatory drug (NSAID), was orally administered was used as a control group.

TABLE 1

| Groups | Compositions (mg) | | |
|---|---|---|---|
| | IND | MF | EC |
| Controls | | | |
| Intact | 0 | 0 | 0 |
| EPD | 0 | 0 | 0 |
| Reference | | | |
| IND | 5 | 0 | 0 |

TABLE 1-continued

| Groups | Compositions (mg) | | |
|---|---|---|---|
| | IND | MF | EC |
| Single formula | | | |
| MF | 0 | 200 | 0 |
| EC | 0 | 0 | 200 |
| Mixed formula - MF:EC | | | |
| 1:1 | 0 | 100 | 100 |
| 1:2 | 0 | 67 | 133 |
| 1:4 | 0 | 40 | 160 |
| 1:6 | 0 | 29 | 171 |
| 1:8 | 0 | 22 | 178 |
| 2:1 | 0 | 133 | 67 |
| 4:1 | 0 | 160 | 40 |
| 6:1 | 0 | 171 | 29 |
| 8:1 | 0 | 178 | 22 |

EPD = Experimental periodontitis diseases;
IND = Indomethacin;
MF = *Moringa* Folium(Leaf parts of Drumstick-tree; *Moringa oleifera* Lam.);
EC = Eucommiae Cortex(Stem bark parts of *Eucommia ulmoides* Oliver)

Composition and Administration of Test Substances

An adequate amount of MF or EC was dissolved directly in sterilized distilled water and orally administered at a dosage of 5 mL/kg once a day for 10 days from 24 hours after ligation of the cervical portion. The composition of MF or EC only was dissolved in sterilized distilled water to a concentration of 40 mg/mL and orally administered at a dosage of 5 mL/kg (200 mg/kg). MF:EC complex compositions (1:1, 1:2, 1:4, 1:6, 1:8, 2:1, 4:1, 6:1 and 8:1) were prepared by dissolving MF and EC (100:100, 66:134, 40:160, 28:172, 22:178, 134:66, 160:40, 172:28 and 178:22 mg:mg) in 5 mL of distilled water and orally administered at a dosage of 5 mL/kg (200 mg/kg). Also, IND was dissolved in sterilized distilled water to a concentration of 1 mg/mL and orally administered at a dosage of 5 mL/kg (5 mg/kg) once a day for 10 days from 24 hours after ligation of the cervical portion. For a normal control group and an EPD control group, only the sterilized distilled water was orally administered instead of the natural substance extract or IND with the same dosage and frequency to apply the same stress.

Induction of Periodontal Disease

According to the method previously reported by the inventors of the present invention [Lee et al., 2014; Park et al., 2016], the experimental animals were accustomed to the laboratory environment for 10 days and generally inhalation anesthetized with a mixture gas of 3% isoflurane (Nana Pharm. Co., Hwasung, Korea), 70% $N_2O$ and 28.5% $O_2$ using an inhaler (Surgivet, Waukesha, Wis., USA) and a ventilator (Model 687, Harvard Apparatus, Cambridge, UK). The cervical portion of the left incisor was ligated with 3-0 nylon suture to induce periodontitis and gingiva. For a normal control group, the cervical portion of the incisor was not ligated.

Investigation of Weight Gain

For measurement of weight gain, the change in body weight was measured throughout the experiment period using an electronic scale. The weight gain was measured by measuring body weight on the first day of sample administration 1 day after the ligation and on the final day of sample administration 10 days later.

Weight gain=body weight on the day of scarification−body weight at the beginning of sample administration(24 hours after the ligation).

Investigation of Change in Interleukin (IL)-1β and TNF-α in Gingival Tissue

After EPD for 11 days, the gingival tissue was homogenized and subjected to measurement with the IL-1β and TNF-α rat ELISA kits (Abcam, Cambridge, UK). The experiment was conducted according to the manufacturer's instructions. 100 μL of the homogenized sample and reference standard were added to each well and then incubated in a 37° C. incubator for 2 hours. After removing the supernatant and adding 100 μL of a 1× biotin-conjugated antibody to each well, incubation was conducted in a 37° C. incubator for 1 hour. After removing the supernatant from each well and washing 3 times, 100 μL of 1× horseradish peroxidase-conjugated avidin was added and incubation was conducted at 37° C. for an hour. After adding 90 μL of 3, 3', 5, 5'-tetramethylbenzidine to each well, incubation was conducted at 37° C. for 15-30 minutes. After adding 50 μL of a stop solution to each well, absorbance was measured with a microplate reader (Tecan, Mannedofr, Switzerland) at a wavelength of 450 nm.

Investigation of MDA Content

For measurement of the lipid peroxidation marker MDA, gingival tissue was detached from the portion adjacent to the ligated portion of the tooth and homogenized with a homogenizer by adding to a 50 mM Tris-HCl, 0.1 mM EGTA and 1 mM phenylmethylsulfonyl fluoride (pH 7.4) buffer. 200 μL of a reaction mixture (8.1% (w/v) sodium dodecyl sulfate, 1500 μL of 20% (v/v) acetic acid, 1500 μL of 0.8% (w/v) thiobarbituric acid and 700 μL of DW) was added to 100 μL of the homogenized gingival tissue. After incubation at 95° C. for 1 hour and conducting centrifugation at 3000×g for 10 minutes, the absorbance of the supernatant was measured at 650 nm using a UV/VIS spectrophotometer.

Measurement of Number of Osteoclasts

The number of osteoclasts was determined by staining with TRAP and counting the number of TRAP-positive multinucleated cells. The TRAP staining was conducted using the TRAP staining kit (Sigma-Aldrich, St. Louis, Mo., USA) according to the manufacturer's instructions. Following deparaffinization and hydration, the slide was immersed in a fixative solution (25 mL of a citrate solution, 65 mL of acetone, and 8 mL of 37% formaldehyde) for 30 seconds and then washed with running water for 10 minutes. After dropping a mixture solution of 45 mL of distilled water, 0.5 mL of a fast garnet GBC solution, 0.5 mL of a sodium nitrite solution, 0.5 mL of naphthol AS-BI, 2 mL of an acetate solution and 1 mL of a tartrate solution on the slide glass at 37° C., incubation was conducted for about 16 hours on average in a humid chamber at 37° C. Then, after washing with 100% alcohol, staining was performed with methyl green for 1 hour for counterstaining. The number of TRAP-positive multinucleated osteoclasts (having 3 or more nuclei) formed on the surface of the alveolar bone was counted using an optical microscope.

Investigation of Change in Alveolar Bone Volume

Alveolar bone loss was measured according to the method of Crawford et al. [1987]. The rat was sacrificed 10 days after the sample administration (11 days after EPD 11) and the teeth and the gingiva were exposed as much as possible. The area between the end of the gingiva and the end of the incisor between the two teeth subjected to EPD was expressed as mm/rat.

Measurement of Change in Number of Viable Aerobic Bacteria

For counting of the viable aerobic bacteria, the ligated left incisor was pull out and the periodontal tissue was taken and immersed in 0.3 mL of a brain heart infusion broth (BHI, Becton, Dickenson and Company, USA). The tissue was homogenized, diluted to 1:100 and 1:1000 and then inoculated to blood agar. After incubating at 37° C. for 48 hours under the condition of 5% $CO_2$, the number of colonies was counted and the number of viable bacteria was calculated.

Number of viable bacteria=the number of colonies× $10^5$ CFU/g tissue.

Figure 3:
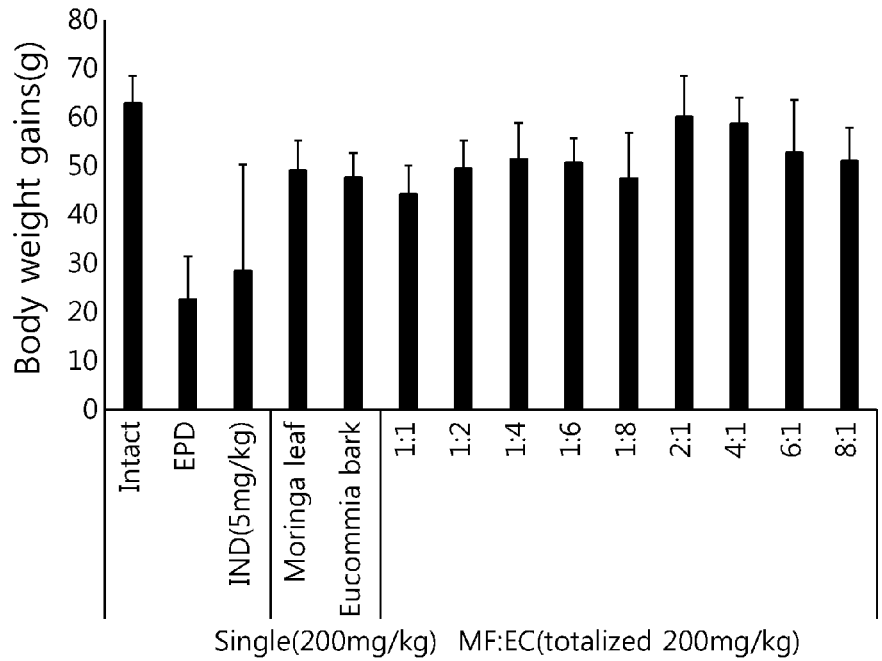
FIG. 3 shows a result of investigating gingivitis- and periodontitis-improving effect by measuring the change in body weight depending on the mixing ratio of a *moringa* leaf extract and a *eucommia* bark extract.

2.1.2.1. Change in Body Weight of Periodontal Disease-induced Model (FIG. 3)

For the EPD control group, significant ($p<0.05$) decrease in body weight as compared to the normal control group was confirmed from 7 days after the ligation (6 days after the beginning of administration) and significant ($p<0.01$) decrease in weight gain was also observed throughout the 10-day administration period as compared to the normal control group. Meanwhile, for the groups administered with the MF and EC compositions alone and MF:EC 1:1 and 8:1 complex compositions, significant ($p<0.01$ or $p<0.05$) increase in body weight as compared to the EPD control group was confirmed from 8 days after the beginning of the administration. Also, significant ($p<0.01$ or $p<0.05$) increase in body weight as compared to the EPD control group was confirmed from 6 days after the beginning of the administration for the groups administered with MF:EC 4:1 and 6:1 complex compositions, from 7 days after the beginning of the administration for the groups administered with MF:EC 1:2, 1:4 and 2:1 complex compositions, from 9 and 10 days after the beginning of the administration for the groups administered with MF:EC 1:6 and 1:8 complex compositions, respectively. All the groups administered with MF and EC alone or the complex compositions showed significant ($p<0.01$) increase in weight gain as compared to the EPD control group.

Figure 4:
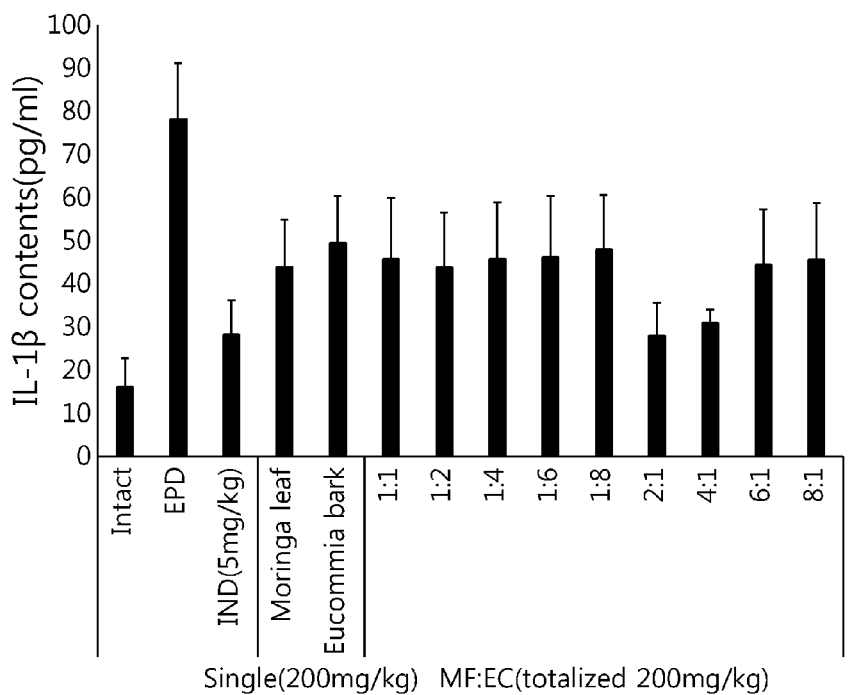
FIG. 4 shows a result of investigating gingivitis- and periodontitis-improving effect by measuring the content of the inflammation marker IL-1β in the gingival tissue depending on the mixing ratio of a *moringa* leaf extract and a *eucommia* bark extract.

2.1.2.2. Investigation of Gingivitis- and Periodontitis-improving Effect Through Change in IL-1β Content in Gingival Tissue of Periodontal Disease-induced Model (FIG. 4)

For the EPD control group, significant ($p<0.01$) increase in the IL-1β content in the gingival tissue was acknowledged as compared to the normal control group. For all the test groups including the group administered with 200 mg/kg EC composition only, significant ($p<0.01$) decrease in the IL-1β content was acknowledged as compared to the EPD control group. In particular, the groups administered with MF:EC 2:1 and 4:1 complex compositions showed significant ($p<0.01$ or $p<0.05$) decrease in the IL-1β content in the gingival tissue as compared to the groups administered with the MF and EC compositions alone.

Figure 5:
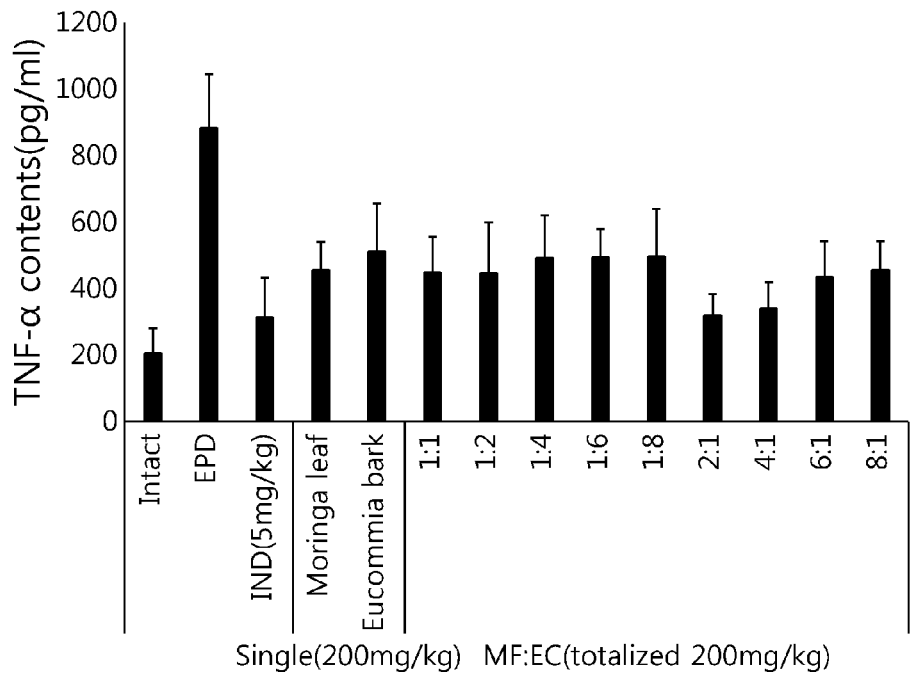
FIG. 5 shows a result of investigating gingivitis- and periodontitis-improving effect by measuring the content of the inflammation marker TNF-α in the gingival tissue depending on the mixing ratio of a *moringa* leaf extract and a *eucommia* bark extract.

2.1.2.3. Investigation of Gingivitis- and Periodontitis-improving Effect Through Change in TNF-α Content in Gingival Tissue of Periodontal Disease-induced Model (FIG. 5)

For the EPD control group, significant ($p<0.01$) increase in the TNF-α content in the gingival tissue was acknowledged as compared to the normal control group. For all the test groups including the group administered with 200 mg/kg MF:EC 1:1 complex composition, significant ($p<0.01$) decrease in the TNF-α content was acknowledged as compared to the EPD control group. In particular, the groups administered with MF:EC 2:1 and 4:1 complex compositions showed significant ($p<0.01$ or $p<0.05$) decrease in the TNF-α content in the gingival tissue as compared to the groups administered with the MF and EC compositions alone.

Figure 6:
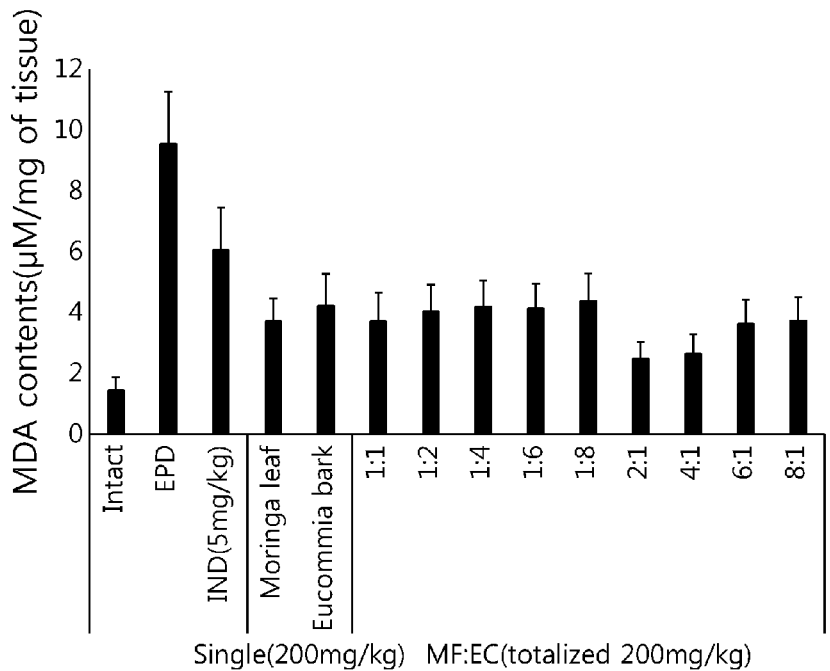
FIG. 6 shows a result of investigating gingivitis- and periodontitis-improving effect by measuring the content of MDA exhibiting antioxidant effect in the gingival tissue depending on the mixing ratio of a *moringa* leaf extract and a *eucommia* bark extract.

2.1.2.4. Investigation of Gingivitis- and Periodontitis-improving Effect by Antioxidation Through Change in MDA Content in Gingival Tissue of Periodontal Disease-Induced Model (FIG. 6)

For the EPD control group, significant ($p<0.01$) increase in the MDA content in the gingival tissue was acknowledged as compared to the normal control group. For all the test groups including the group administered with 200 mg/kg MF:EC 1:2 complex composition, significant ($p<0.01$) decrease in the MDA content was acknowledged as compared to the EPD control group. In particular, the groups administered with MF:EC 2:1 and 4:1 complex compositions showed significant ($p<0.01$ or $p<0.05$) decrease in the MDA content in the gingival tissue as compared to the groups administered with the MF and EC compositions alone.

Figure 7:
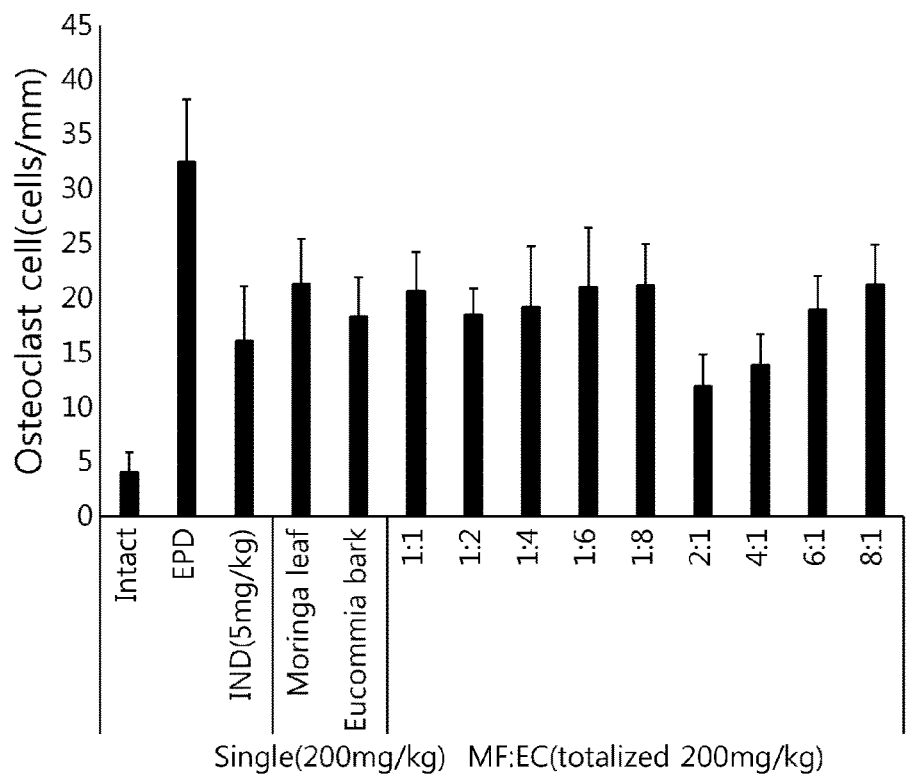
FIG. 7 shows a result of investigating gingivitis- and periodontitis-improving effect by measuring the number of osteoclasts in alveolar bone depending on the mixing ratio of a *moringa* leaf extract and a *eucommia* bark extract.

2.1.2.5. Investigation of Gingivitis- and Periodontitis-improving Effect Through Measurement of Number of Osteoclasts in Alveolar Bone in Periodontal Disease-induced Model (FIG. 7)

The EPD control group showed 715.63% of change in the number of osteoclasts as compared to the normal control group. Meanwhile, the groups administered with IND, MF and EC compositions alone and MF:EC 1:1, 1:2, 1:4, 1:6, 1:8, 2:1, 4:1, 6:1 and 8:1 complex compositions with a dosage of 200 mg/kg showed change of −50.19, −34.48, −43.68, −36.40, −43.30, −41.00, −35.63, −34.87, −63.22, −57.09, −41.76 and −34.48%, respectively, as compared to the EPD control group.

Figure 8:
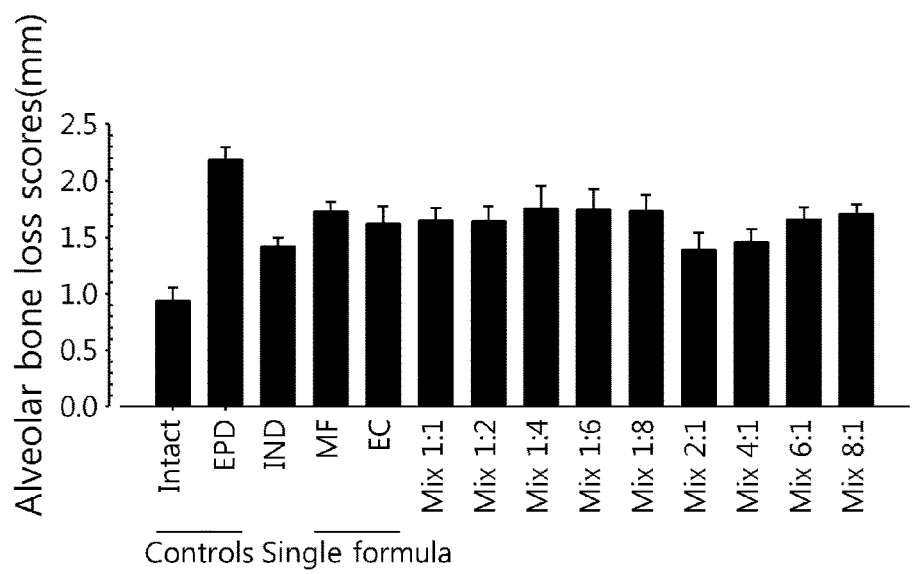
FIG. 8 shows a result of investigating gingivitis- and periodontitis-improving effect by investigating the effect of inhibiting alveolar bone loss and regenerating alveolar bone through measurement of alveolar bone volume depending on the mixing ratio of a *moringa* leaf extract and a *eucommia* bark extract.

2.1.2.6. Investigation of Gingivitis- and Periodontitis-improving Effect Through Measurement of Change in Alveolar Bone Volume of Periodontal Disease-induced Model (FIG. 8)

For the EPD control group, significant ($p<0.01$) decrease in the alveolar bone volume was acknowledged as compared to the normal control group. For all the test groups including the group administered with 200 mg/kg MF:EC 6:1 complex composition, significant ($p<0.01$) increase in the alveolar bone volume was acknowledged as compared to the EPD control group. In particular, the groups administered with MF:EC 2:1 and 4:1 complex compositions showed significant ($p<0.01$ or $p<0.05$) decrease in the alveolar bone volume as compared to the groups administered with the MF and EC compositions alone.

Figure 9:
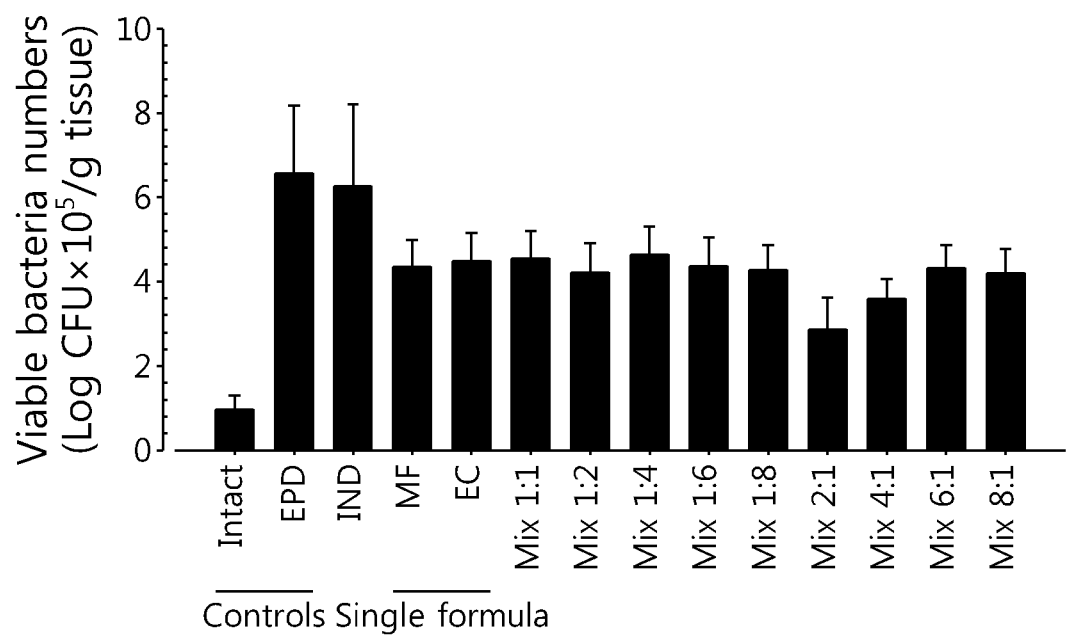
FIG. 9 shows a result of investigating gingivitis- and periodontitis-improving effect through antibiosis by measuring the number of total viable aerobic bacteria in the buccal groove depending on the mixing ratio of a *moringa* leaf extract and a *eucommia* bark extract.

2.1.2.7. Investigation of Gingivitis- and Periodontitis-improving Effect Through Measurement of Number of Total Viable Aerobic Bacteria in Buccal Groove of Periodontal Disease-induced Model (FIG. 9)

For the EPD control group, significant ($p<0.01$) increase in the number of total viable aerobic bacteria in the buccal groove was acknowledged as compared to the normal control group. For all the test groups excluding the group administered with 5 mg/kg IND, which showed similar number of viable bacteria as the EPD control group, significant ($p<0.01$) decrease in the number of viable bacteria was acknowledged as compared to the EPD control group. In particular, the groups administered with MF:EC 2:1 and 4:1 complex compositions showed significant ($p<0.01$ or $p<0.05$) decrease in the number of total viable aerobic bacteria in the buccal groove as compared to the groups administered with the MF and EC compositions alone.

What is claimed is:

1. A method of improving or treating a periodontal disease in an individual, comprising administering a composition comprising a *moringa* extract and a *eucommia* bark extract as active ingredients to the individual,
    wherein a weight ratio of the *moringa* extract and the *eucommia* bark extract is 2:1 to 4:1 (*moringa* extract: *eucommia* bark extract).

2. The method according to claim 1, wherein the composition is a food or pharmaceutical composition.

3. The method according to claim 1, wherein the *moringa* extract is a *moringa* leaf extract.

4. The method according to claim 1, wherein the *moringa* extract and the *eucommia* bark extract are prepared by using water, a $C_1$-$C_4$ lower alcohol or a mixture thereof as an extraction solvent.

5. The method according to claim 1, wherein the periodontal disease is gingivitis or periodontitis.

6. The method according to claim 1, wherein the composition further comprises one or more extract selected from a group consisting of pomegranate, balloon flower root, *gardeniae* fructus, *scutellariae* radix, lotus leaf, Chinese mulberry leaf, ginger, peony root, *achyranthis* radix, red clover, dandelion and dandelion root extracts as an active ingredient.

7. The method according to claim 6, wherein the pomegranate extract comprises 0.5-3 mg/g of ellagic acid.

8. The method according to claim 6, wherein the balloon flower root, *gardeniae* fructus, *scutellariae* radix, lotus leaf, Chinese mulberry leaf, ginger, peony root, *achyranthis* radix, red clover, dandelion and dandelion root extracts are prepared by using water, a $C_1$-$C_4$ lower alcohol or a mixture thereof as an extraction solvent.

* * * * *